United States Patent
Risch

(10) Patent No.: US 12,269,218 B2
(45) Date of Patent: Apr. 8, 2025

(54) METHOD FOR MOUNTING AN X-RAY MARKER IN AN IMPLANT

(71) Applicant: BIOTRONIK AG, Bülach (CH)

(72) Inventor: Fabian Risch, Doerflingen (CH)

(73) Assignee: BIOTRONIK AG, Buelach (CH)

(*) Notice: Subject to any disclaimer, the term of this patent is extended or adjusted under 35 U.S.C. 154(b) by 438 days.

(21) Appl. No.: 17/624,908

(22) PCT Filed: Jun. 16, 2020

(86) PCT No.: PCT/EP2020/066595
§ 371 (c)(1),
(2) Date: Jan. 5, 2022

(87) PCT Pub. No.: WO2021/004734
PCT Pub. Date: Jan. 14, 2021

(65) Prior Publication Data
US 2022/0274345 A1    Sep. 1, 2022

(30) Foreign Application Priority Data

Jul. 11, 2019 (EP) .................................. 19185654

(51) Int. Cl.
*B29C 65/20* (2006.01)
*A61B 90/00* (2016.01)
(Continued)

(52) U.S. Cl.
CPC .............. *B29C 65/20* (2013.01); *A61B 90/39* (2016.02); *A61F 2/82* (2013.01); *B29C 65/44* (2013.01);
(Continued)

(58) Field of Classification Search
CPC ................ A61F 2/82; A61F 2220/0033; A61F 2240/001; A61F 2250/0098; B29C 66/742;
(Continued)

(56) References Cited

U.S. PATENT DOCUMENTS

| | | |
|---|---|---|
| 2009/0204203 A1 | 8/2009 | Allen et al. |
| 2016/0120671 A1 | 5/2016 | Higashi et al. |
| 2016/0228267 A1 | 8/2016 | Pacetti et al. |

FOREIGN PATENT DOCUMENTS

| | | |
|---|---|---|
| JP | 2018517496 A | 7/2018 |
| JP | 2018121936 A | 8/2018 |

(Continued)

OTHER PUBLICATIONS

International Search Report and Written Opinion from the corresponding International Patent Application No. PCT/EP2020/066595, dated Jul. 31, 2020.
(Continued)

*Primary Examiner* — Monica A Huson
(74) *Attorney, Agent, or Firm* — Greer, Burns & Crain, Ltd.; Steven P. Fallon

(57) ABSTRACT

A method for connecting an X-ray marker to a base body of an implant is provided. The based body includes a receptacle for receiving an X-ray marker. A flexible film and an X-ray marker are arranged so that at least a section of the film is located between the receptacle and the X-ray marker. The X-ray marker is pressed into the receptacle while interposing the film so that the X-ray marker is plastically deformed and, together with the film, is fixed in a force-fit manner in the receptacle. The film prevents contact between the X-ray marker and the base body.

18 Claims, 7 Drawing Sheets

(51) Int. Cl.
  *A61F 2/82* (2013.01)
  *B29C 65/00* (2006.01)
  *B29C 65/44* (2006.01)
  *A61B 17/00* (2006.01)
  *B29L 31/00* (2006.01)
(52) U.S. Cl.
  CPC .......... *B29C 66/712* (2013.01); *B29C 66/742* (2013.01); *A61B 2017/00526* (2013.01); *A61B 2090/3966* (2016.02); *A61F 2220/0033* (2013.01); *A61F 2240/001* (2013.01); *A61F 2250/0098* (2013.01); *B29L 2031/7532* (2013.01)
(58) Field of Classification Search
  CPC ....... B29C 65/44; B29C 66/712; B29C 65/20; A61B 90/39; A61B 2017/00526; A61B 2090/3966; B29L 2031/7532
  See application file for complete search history.

(56) References Cited

FOREIGN PATENT DOCUMENTS

| | | | |
|---|---|---|---|
| JP | 2019150077 A | * 9/2019 | ............... A61F 2/82 |
| WO | 2016201317 A1 | 12/2016 | |
| WO | 2018016259 A1 | 1/2018 | |
| WO | 2018153300 A1 | 8/2018 | |

OTHER PUBLICATIONS

Japanese Office Action from the corresponding Japanese Patent Application No. 2021-568272, dated Mar. 15, 2024.
Japanese Office Action from the corresponding Japanese Patent Application No. 2021-568272, dated Aug. 19, 2024.

* cited by examiner

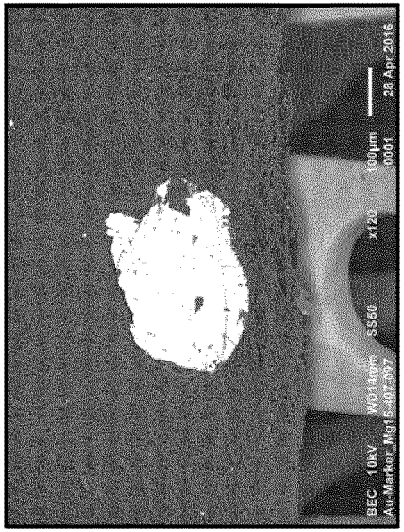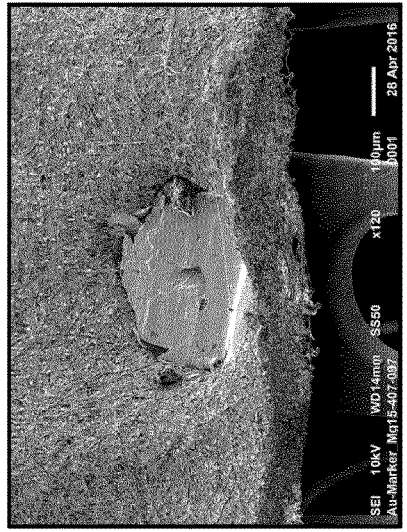
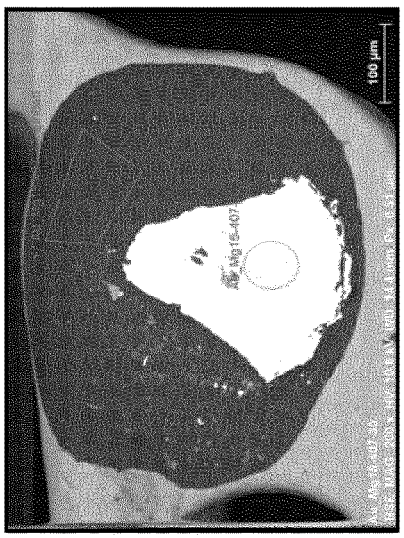
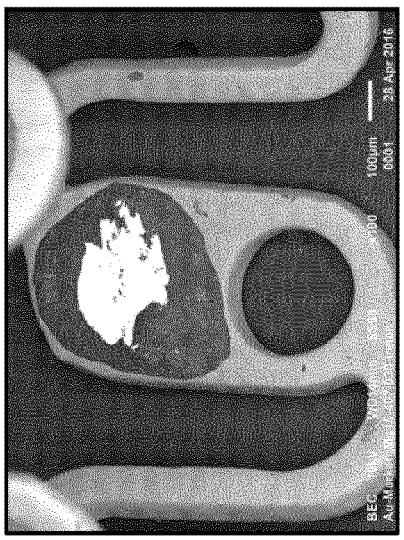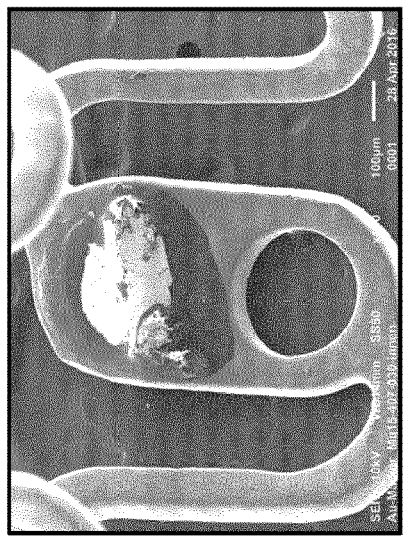
FIG. 7A    FIG. 7B    FIG. 7C

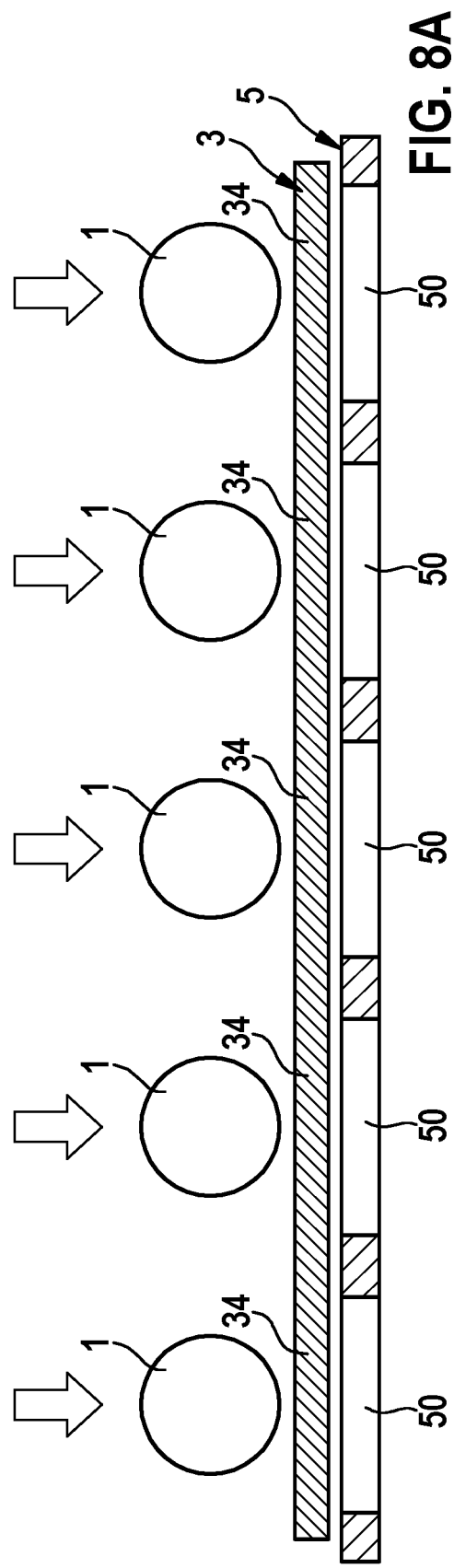
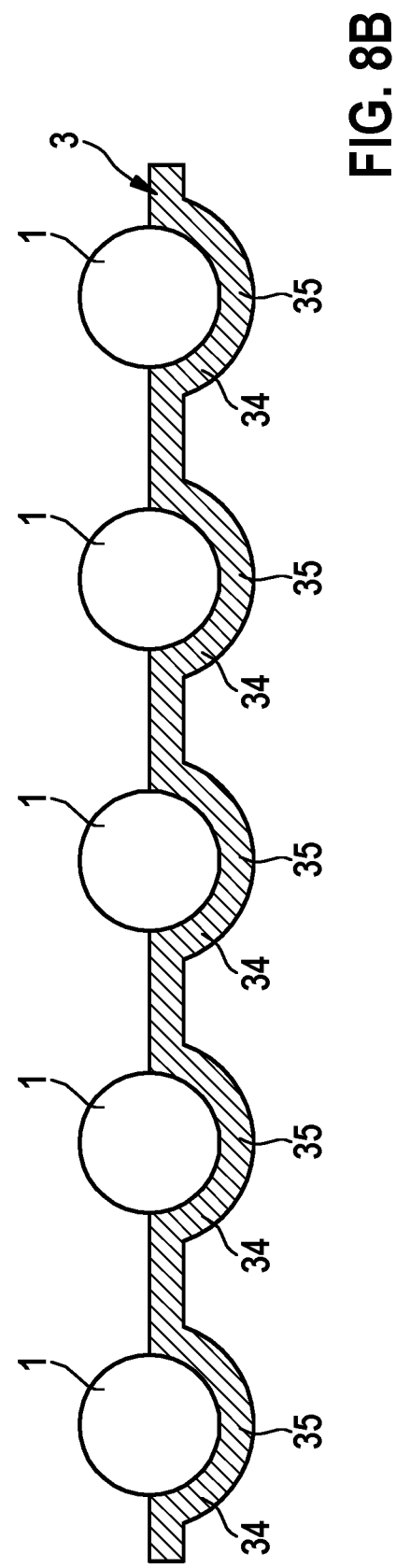

METHOD FOR MOUNTING AN X-RAY MARKER IN AN IMPLANT

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2020/066595, which was filed Jun. 16, 2020, which application claimed priority from European Application Serial Number 19185654.1, which was filed Jul. 11, 2019.

FIELD OF THE INVENTION

A field of the invention is X-Ray marker for implants, e.g., stents and valves. Particular additional example implants include occluders, filters, heart valve prostheses (in particular stent-based aortic valve prostheses) or other vessel support devices

BACKGROUND

In such methods, the X-ray marker has previously been connected to the stent by way of adhesion or pressing, for example.

In the case of adhesion, problems arise that, on the one hand, it is difficult to precisely meter a comparatively small amount of adhesive and, on the other hand, the exact positioning of the adhesive amount presents another challenge. In principle, the problem with adhesion is further a limited processing duration (pot life). Moreover, when using solvent-based adhesives, it must be ensured that these do not adversely affect the implant or the stent.

Furthermore, the problem in the case of pressing is essentially that frequently X-ray markers made of noble metals (such as gold or platinum, or the like) are used, which in combination with a base body of the stent made of a base metal create contact erosion. Especially on biodegradable stents, this can result in an undesirable acceleration of the degradation. Additionally, the X-ray marker can work its way out of the stent, so that direct contact between the X-ray marker and the base body has to be prevented. This applies to all joining methods with direct contact (such as joining by screws, riveting, and the like).

US 2016/0228267 discloses a method for pressing an X-ray marker into a stent, wherein a space between the X-ray marker and the stent can be filled with a polymer when the stent is coated.

SUMMARY OF THE INVENTION

Methods of the invention connect an X-ray marker in a simple and reliable manner to an implant in a manner where potential contact corrosion is to be avoided from the outset. In preferred methods, no adhesive bond needed.

A preferred method for connecting an X-ray marker to a base body of an implant includes providing a base body including a receptacle for receiving an X-ray marker. A flexible film and an X-ray marker are arranged so that at least a section of the film is located between the receptacle and the X-ray marker. The X-ray marker and the section of the film are pressed into the receptacle, so that the X-ray marker is plastically deformed and, together with the film, is fixed in a force-fit manner in the receptacle, with the film preventing contact between the X-ray marker and the base body.

BRIEF DESCRIPTION OF THE DRAWINGS

Embodiments of the invention and further features and advantages will be described hereafter based on the figures. In the drawings:

FIG. 5 shows the X-ray marker pressed into the through-opening of the base body, a section of the film protruding from the through-opening after being pressed in;

FIG. 7A shows SEM images of a pressed-in X-ray marker made of gold in a film made of electrospun polyurethane;

FIG. 7B shows SEM images of a pressed-in X-ray marker in fused polyurethane in a view from outside the base body;

FIG. 7C shows SEM images of a pressed-in X-ray marker in fused polyurethane in a view from inside the base body;

FIGS. 8A-8C show schematic sectional views of the pre-mounting of X-ray markers on a film over a perforated plate.

DETAILED DESCRIPTION OF THE PREFERRED EMBODIMENTS

Figure 1A:
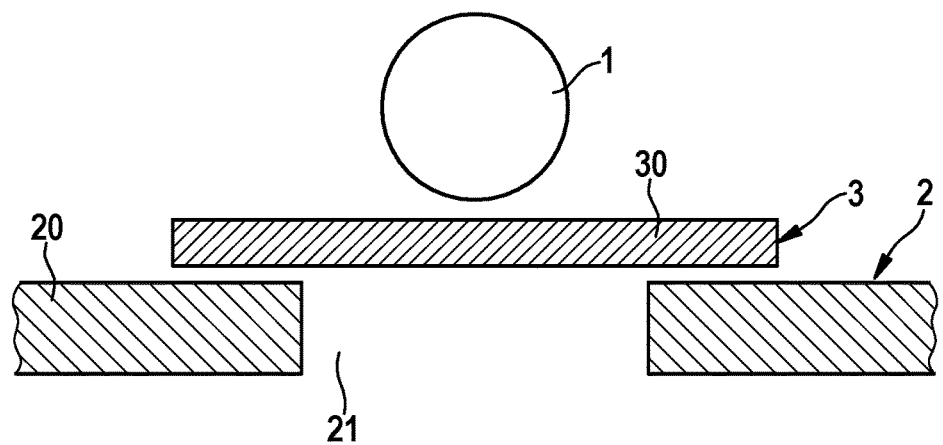
FIG. 1A shows a schematic sectional view of a section of a base body of a stent including a through-opening, a spherical X-ray marker being arranged above the through-opening, and a film being arranged between the marker and the base body, which is to be pressed into the through-opening together with the marker.

With preferred methods, a connection between the X-ray marker and the base body of the implant is sufficiently elastic in the process to be able to compensate for a minor deformation of the base body of the implant. Moreover, the pressing-in operation can advantageously be configured in such a way that the wall thickness of the base body is not increased by the pressed-in X-ray marker.

The receptacle is preferably designed as a cavity, or particularly preferably as a through-opening.

The base body can include a plurality of mutually connected struts, which form a circumferential lattice structure. Such a base body can be provided by cutting individual regions out of a tubular blank, for example by way of a laser. According to a particularly preferred embodiment, the base body is made of a magnesium alloy, and in particular a Mg—Zn—Ca, Mg—Zn—Al or Mg—Al alloy.

According to one embodiment of the method, it is provided that the X-ray marker is pressed into the cavity or the through-opening, while interposing the film, in such a way that the X-ray marker, with a circumferential outer side, makes contact with the film, which, in turn, rests against a circumferential inner side of the cavity or of the through-opening, so that a circumferential section of the film is arranged between the X-ray marker and the base body.

Within the scope of the present application, a cavity shall be understood to mean any at least one-sided opening in the base body of the implant.

According to one embodiment of the method, it is further provided that the X-ray marker, after having been pressed into the cavity/the through-opening, has a surface that extends along the opening plane of the cavity/of the through-opening and is covered by a section of the film, which is connected to the circumferential section of the film which is pressed into the through-opening. In other words, the X-ray marker, after having been pressed in, is thus embedded into the film, wherein only a further surface of the X-ray marker, which faces away from the surface covered with the film, is exposed.

According to one embodiment of the method, it is further provided that a section of the film protruding from the cavity/the through-opening is cut off, so that the circumferential section of the film, on one side of the base body, preferably ends or is arranged flush with a surface of the base body.

According to another embodiment of the method, it is provided that the protruding section of the film is removed or cut off by way of a stamping action during the pressing-in operation. According to an alternative embodiment of the method, it is provided that the protruding section of the film is removed or cut off, for example by trimming, subsequently for the pressing-in operation.

According to an alternative embodiment of the method according to the invention, it is provided that the film is dimensioned in such a way that, after the X-ray marker has been pressed into the base body, the film, on one side of the base body, does not protrude from the cavity/the through-opening.

According to one embodiment of the method, it is further provided that the X-ray marker is spherical or cylindrical prior to being pressed into the through-opening. According to one embodiment of the method, it is further provided that the X-ray marker, after having been pressed into the cavity/the through-opening, is half shell-shaped/disk-shaped as a result of the plastic deformation thereof and, with the two surfaces thereof facing away from one another is preferably designed to be flush with an adjoining surface of the base body.

Two pressing jaws can be used to press in the X-ray marker, wherein the X-ray marker, together with the film, is arranged between the pressing jaws, and the pressing jaws are moved toward one another for pressing the X-ray marker and the film into the cavity/the through-opening, so that the at least one X-ray marker is plastically deformed by the pressing jaws engaging on both sides and, in the process, is fixed in a force-fit manner in the cavity/the through-opening. According to one embodiment, the movement of the pressing jaws toward one another can be controlled in such a way that a final thickness of the at least one X-ray marker in the pressing direction corresponds to a wall thickness of the base body (see above).

The film used is preferably designed to be elastically or plastically deformable so as to be able to absorb forces that arise when the X-ray marker is being pressed in, without tearing.

According to one embodiment of the method, it is provided that the film includes one of the following materials or is made of one of the following materials: a plastic material, a polymer, polyurethane, electrospun plastic, electrospun polyurethane, PTFE, or silicone.

According to one embodiment of the invention, it is further provided that the X-ray marker is made of a metallic material that is more noble than a metallic material of which the base body is made. According to one embodiment, the X-ray marker can be made of one of the following materials or can include one of the following materials: a radiopaque metallic material, gold, a gold alloy, platinum or a platinum alloy.

According to another embodiment of the method, it is provided that the film is fused after the at least one X-ray marker has been pressed in, for example so as to round a cut edge of the film, or so as to distribute the material of the film uniformly in an annular gap around the at least one X-ray marker.

According to one embodiment of the invention, it is further provided that the film is fused as the at least one X-ray marker and the film are being pressed into the cavity/the through-opening.

For this purpose, for example, the pressing jaws by way of which the at least one X-ray marker and the film are pressed into the through-opening can be heated.

According to another embodiment of the method, it is provided that the X-ray marker, or multiple X-ray markers, and the film are prefabricated.

According to one embodiment of the method, it is provided in this regard that the flexible film and the X-ray marker are provided, prior to being pressed in, in that the X-ray marker, along with further X-ray markers, is arranged on a film and suitably fixed there. Thereafter, the individual X-ray markers can be pressed in.

According to one embodiment, it is provided in this regard that the flexible film and the X-ray marker are provided, prior to being pressed in, in that the film is arranged on a perforated plate including a plurality of holes, wherein the X-ray marker and further X-ray markers are arranged on a respective film section covering a hole and are fixed there, wherein a curvature is imparted to the respective film section as a result of the hole of the perforated plate arranged therebeneath, wherein a curvature of a film section, including the X-ray marker fixed thereon, is arranged in the at least one through-opening before the X-ray marker is pressed into the cavity/the through-opening of the base body.

According to another alternative embodiment of the method, it is provided that the flexible film and the X-ray marker are provided, prior to being pressed in, in that the X-ray marker and further X-ray markers are arranged next to one another and coated with a plastic material, preferably polyurethane, using electrospinning for forming the film.

Electrospinning shall be understood to mean the creation of thin plastic or polymer fibers from a plastic or polymer solution in an electric field. The solution can be accelerated for this purpose between an electrode and a counter electrode, wherein the solution is processed into minute fibers in a complex process, which ultimately deposit on the counter electrode, with the X-ray markers being able to function as the counter electrode in the process so that these can be directly coated with the film material using electrospinning.

According to another alternative embodiment of the method, it is provided that the flexible film and the X-ray marker are provided, prior to being pressed in, in that the X-ray marker and further X-ray markers are arranged between two layers of the film forming the film and are fixed to the film.

Another aspect of the present invention relates to an implant, in particular a stent, including a base body and an X-ray marker that is arranged in a receptacle, in particular a through-opening, of the base body and connected to the base body by way of the method according to the invention.

The preferred embodiments are described based on the example of an X-ray marker for a stent, without being limited thereto. The invention is used to connect a marker to an arbitrary, in particular biodegradable, implant, such as stents, occluders, filters, heart valve prostheses (in particular stent-based aortic valve prostheses) or other vessel support devices.

Figure 1B:
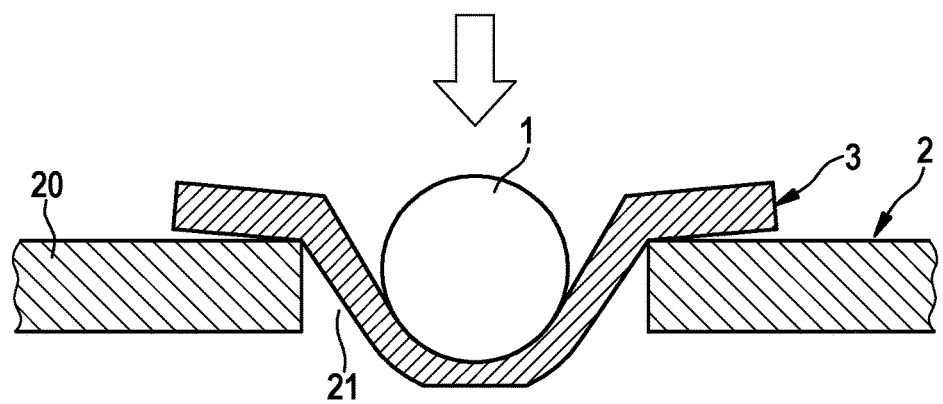
FIG. 1B shows a schematic sectional view of the X-ray marker according to FIG. 1A, which is arranged in the through-opening of the base body together with a section of the film.

FIGS. 1A and 1B, in connection with FIGS. 2 to 6, show an embodiment of a method according to the invention for connecting an X-ray marker 1 to a base body 20 of a stent 2, wherein a base body 20 of a stent 2 is provided, wherein the base body 20 includes a through-opening 21 for receiving the X-ray marker 1, and wherein a flexible film and an X-ray marker 1 are provided, so that at least a section 30 of the film 3 is located between the base body 20 including the through-opening 21 and the X-ray marker 1, and wherein ultimately the X-ray marker 1 is pressed into the through-opening 21 of the base body 20, while interposing the film 3, so that the X-ray marker 1 is plastically deformed and, together with the film 3, is fixed in a force-fit manner in the through-opening 21, wherein the film 3 prevents contact between the X-ray marker 1 and the base body 20, and thereby precludes contact corrosion.

The invention thus describes an alternative mounting option of X-ray markers 1 in stents 2. Conventionally, these are glued in using adhesive dosing. Meanwhile, the present invention allows a plastic or polymer connection to be established between the marker 1 and the base body 20 without the dosing of adhesive.

The film 3 used is preferably accordingly elastically deformable and designed to be able to absorb forces that arise when the marker 1 is being pressed in, without tearing. Electrospun polyurethane, for example, is one film material that has these properties. In principle, all electrospinnable plastic materials may be used, or also single- or multi-layer PTFE or silicone films.

Figure 2:
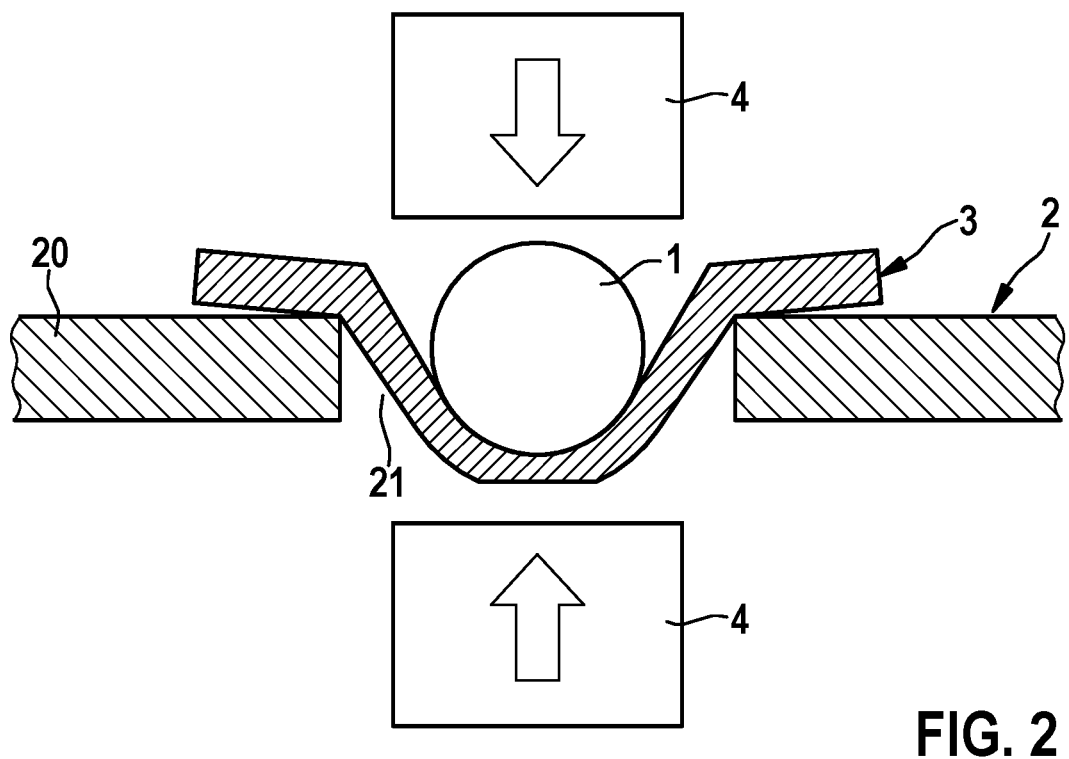
FIG. 2 shows a schematic sectional view of the X-ray marker, the film and the base body, two pressing jaws being displaced toward one another for pressing the X-ray marker into the through-opening together with the film.
Figure 3:
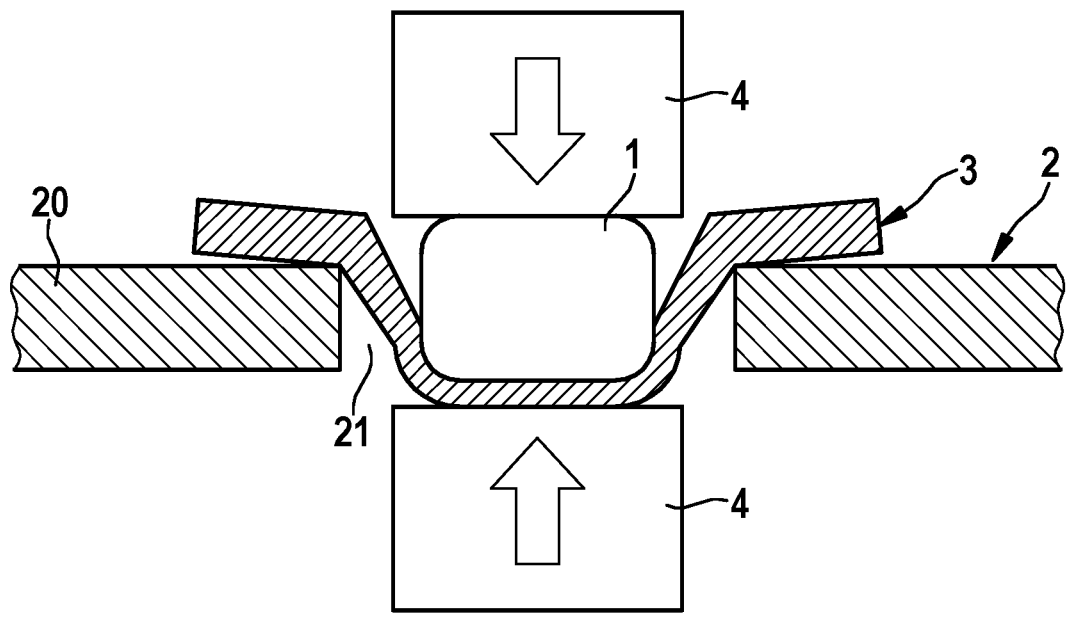
FIGS. 3-4 show the plastic deformation of the X-ray marker according to FIG. 2 by the pressing jaws.
Figure 4:
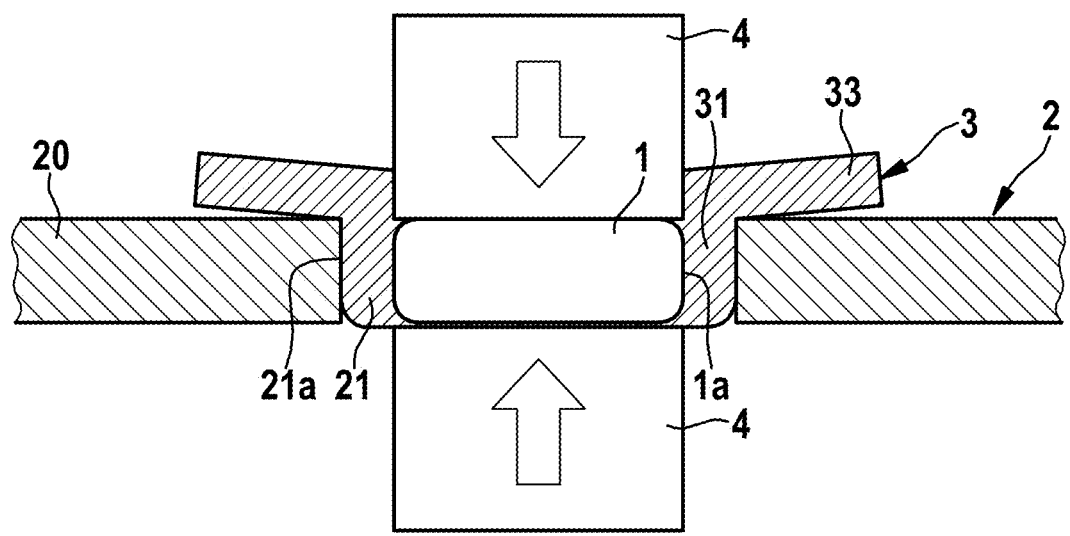
Figure 5:
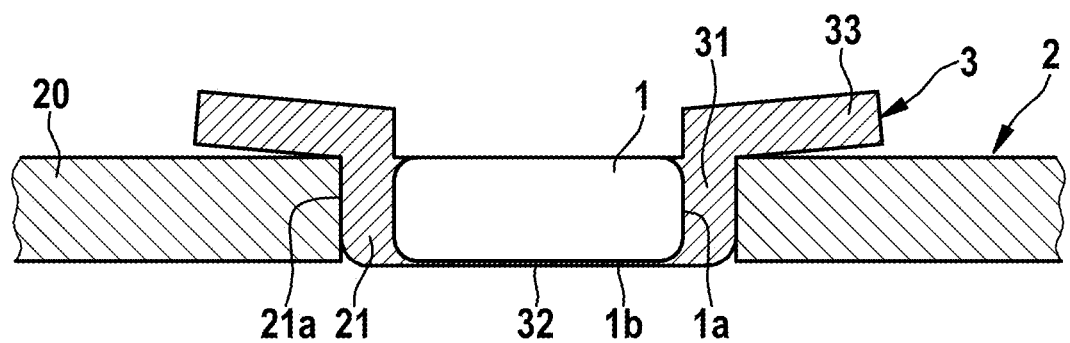

According to FIG. 1A, such a film 3 is placed over a base body 20 of the stent 2. The base body 20 and, in particular, the preformed through-opening or through-openings 21, which are also referred to as marker holes or eyelets, are aligned in such a way that a marker 1 can be positioned in a blind manner from above, which means that the associated through-opening 21 does not need to be visible through the film 3. A film made of electrospun polyurethane is generally not very transparent. As an alternative, a light source, for example, can be placed beneath the through-opening 21. The position of the particular through-opening 21 then becomes visible from the corresponding shadow that is cast. Moreover, a counter plunger can be pushed through the particular through-opening, which then guides the marker 1 during the pressing operation. FIG. 1B shows the X-ray marker 1 arranged in the through-opening 21, together with the film 3, prior to the pressing-in operation, which is illustrated in FIGS. 2 to 4.

Thereafter, the X-ray marker 1, which initially preferably has a spherical shape and can, for example, be made of gold (or another highly radiopaque and soft metal, such as platinum), is pressed, together with the film 3, into the through-opening 21 by way of pressing jaws 4. Using a displacement-controlled movement of the clamping jaws, control is exercised to ensure that the final thickness D of the marker disk 1 corresponds to the wall thickness W of the base body 20 of the stent 2. In this way, it can be ensured that the base body is not damaged by the pressing motion, and also that the X-ray marker or markers 1 does not or do not protrude over the base body edge.

The film 3 can have an appropriate size, so that no protruding film section 33 is present after the pressing operation. Otherwise, the protruding remainder 33 of the film 3 is removed. This can be achieved by a stamping action during pressing or after the pressing-in operation, for example by cutting off the protruding section 33 of the film 3 (see FIGS. 5 and 6).

Figure 6:
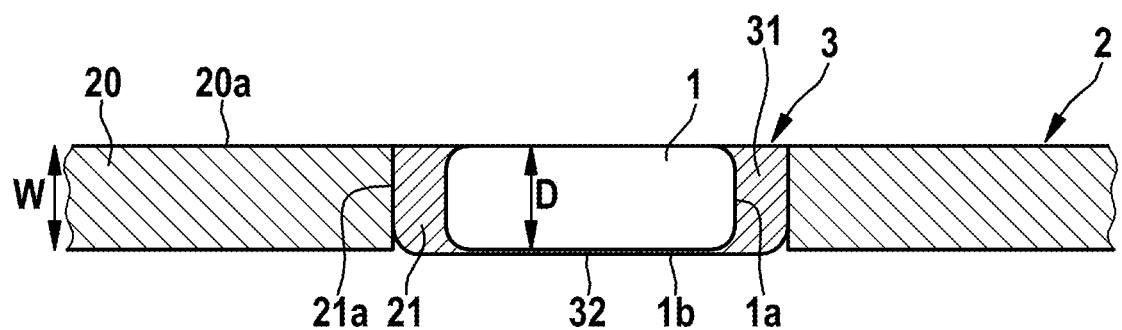
FIG. 6 shows a schematic sectional view of the X-ray marker, the film and the base body after the X-ray marker has been pressed into the through-opening of the base body, the section of the film protruding from the through-opening having been removed.

According to FIG. 6, the X-ray marker is ultimately preferably pressed into the through-opening 21, while interposing the film 3, in such a way that the X-ray marker 1, with a circumferential outer side 1a, makes contact with the film 3, which, in turn, rests against a circumferential inner side 21a of the through-opening 21, so that a circumferential section 31 of the film is arranged between the X-ray marker 1 and the base body 20, or fills a corresponding annular gap between the marker 1 and the base body 20.

According to FIG. 6, it is further provided that, after having been pressed into the through-opening 21, the X-ray marker 1 has a surface 1b that extends along the opening plane of the through-opening 21 and that is covered by a section 32 of the film 3, which is connected to the circumferential section 31 of the film 3 that is pressed into the through-opening 21.

In addition, the pressed-in film 3 can also subsequently be fused. This is done, for example, so as to round a cut edge of the film 3, or so as to evenly distribute the film material (such as the polyurethane) in the annular gap. The fusing can be integrated into the pressing motion, for example by using heatable pressing jaws 4.

For example, flat nose pliers may be used as pressing jaws, having a mechanically limited pressing motion, so that it is not possible to press any further than the wall thickness of the stent. The pressing motion can also be integrated into the existing process step of crimping. Within the scope of the present application, crimping shall be understood to mean the process step during which the stent is arranged around an expansion element (for example a dilatable balloon of a balloon catheter), and the diameter of the stent is reduced to a diameter for insertion into the body. The stent is compressed onto the balloon.

In an alternative embodiment, which is shown by way of example in FIGS. 8A to 9, for example, an assembly is created prior to the actual mounting step, or the step of pressing a marker 1 into an associated through-opening 21 of the base body 20, in which the marker 1 is pre-positioned on the film 3 and, in particular, fixed there.

Figure 8C:
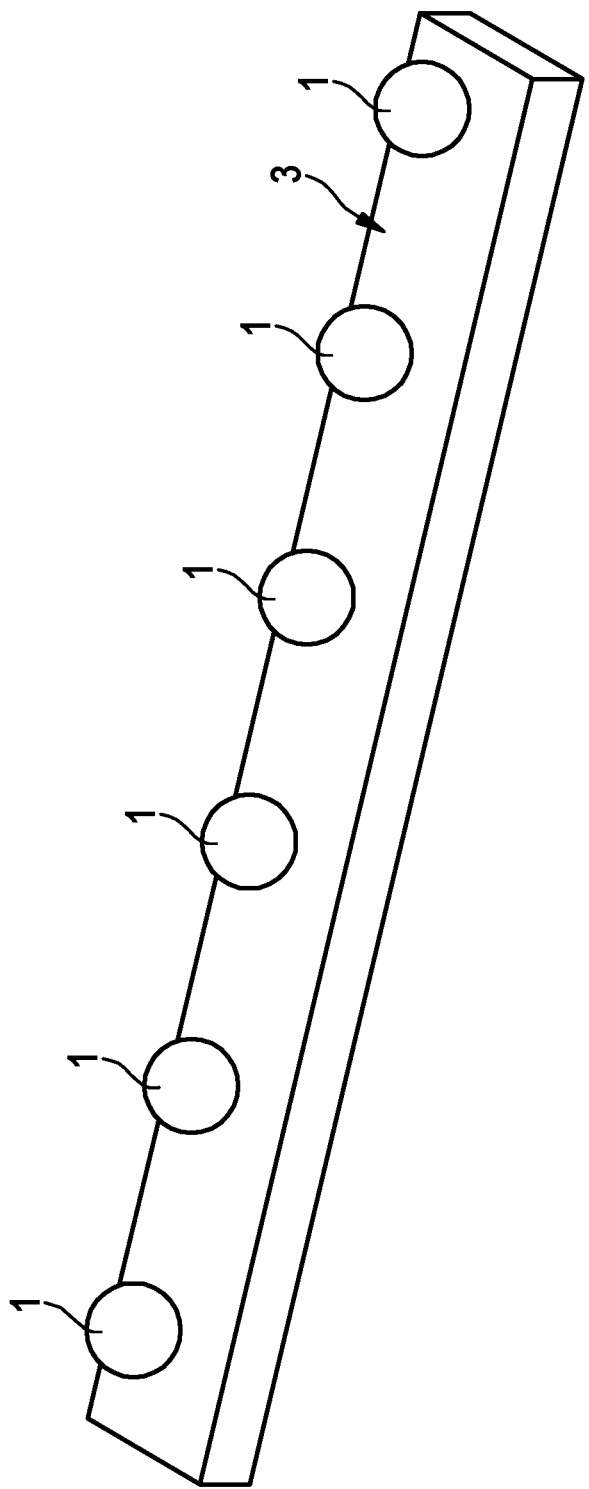

For example, multiple X-ray markers 1 are pre-mounted on a film 3, for example in the form of a film strip 3, over a perforated plate (for example in the form of a perforated metal sheet) (see FIG. 8A), so that a respective X-ray marker 1 is arranged on a film section 34 that covers one hole 50 of the perforated plate 5 and is pressed into the same, whereby a curvature 35 of the film 3 results in each case, which accommodates a marker 1 (see FIGS. 8B and 8C).

Figure 9A:
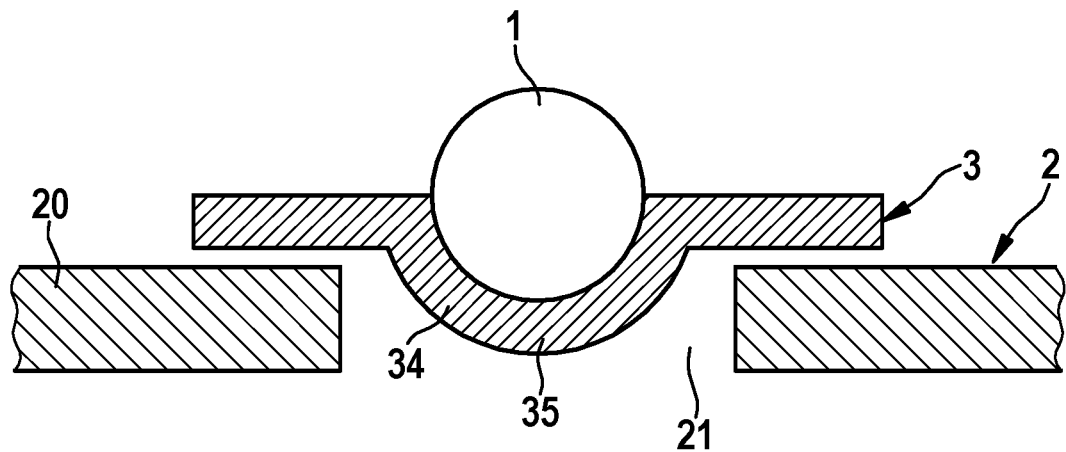
FIGS. 9A-9B show the schematic insertion of the X-ray marker according to FIGS. 8A-8C into the through-opening of a base body.
Figure 9B:
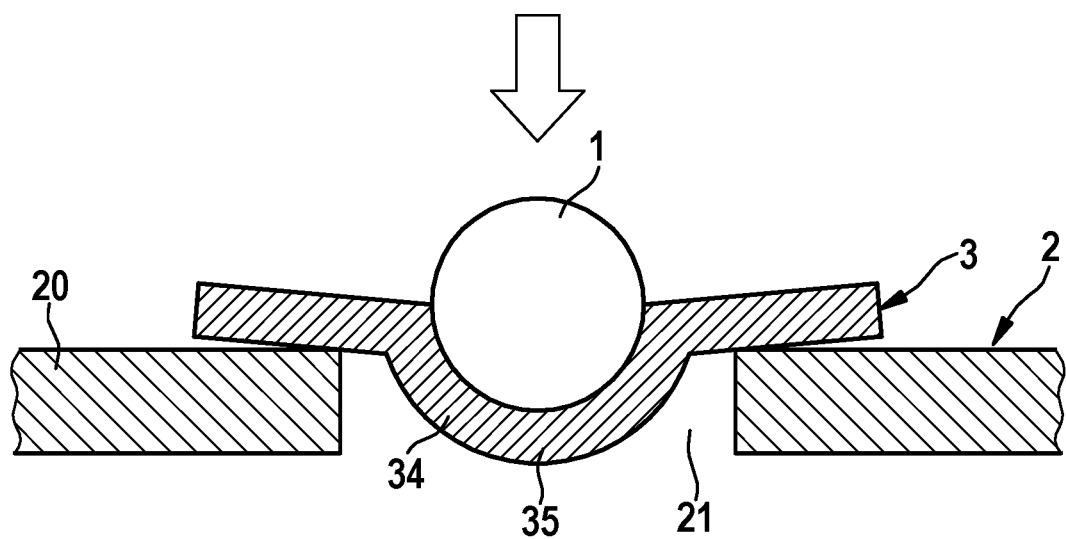

These curvatures 35 can then be positioned particularly easily, in accordance with FIGS. 9A and 9B, in the associated through-opening 21 of the base body 20, together with the respective X-ray marker 1 arranged therein. Thereafter, the pressing operation can be carried out, for example according to FIGS. 2 to 6 (see above).

Moreover, it is possible to create such an assembly including markers 1 and the film 3 by directly coating multiple X-ray markers 1 with a suitable plastic material/polymer (such as polyurethane) by way of electrospinning. As an alternative thereto, the option exists to cover multiple X-ray markers 1 on both sides with a film layer (such as polyurethane), so that the markers 1 are wrapped in a film 3 composed of at least two film layers.

FIGS. 7A to 7C show SEM images of X-ray markers that were pressed into the shown stents using the present invention.

The advantages of the present invention are that adhesive dosing (along with the attendant drawbacks, see above) can be entirely avoided. It is possible to use cost-effective X-ray markers in the original state (spherical) since these do not need to have narrow tolerances. The mounting step can furthermore be integrated into the crimping process.

The invention claimed is:

1. A method for connecting an X-ray marker to a base body of an implant, comprising the following steps:
    providing a base body including a receptacle for receiving an X-ray marker;
    arranging a flexible film and an X-ray marker so that at least a section of the film is located between the receptacle and the X-ray marker; and
    pressing the X-ray marker and the section of the film into the receptacle, so that the X-ray marker is plastically deformed and, together with the film, is fixed in a force-fit manner in the receptacle, with the film preventing contact between the X-ray marker and the base body.

2. The method according to claim 1, wherein the receptacle comprises a cavity or a through-opening.

3. The method according to claim 2, wherein the X-ray marker is shaped such that a circumferential outer side makes contact with the film, which, in turn, rests against a circumferential inner side of the cavity or of the through-opening so that a circumferential section of the film is arranged between the X-ray marker and the base body as a result of the pressing.

4. The method according to claim 3, wherein the X-ray marker is shaped, such that after the pressing, a surface of the X-ray marker extends along the opening plane of the cavity or the through-opening and is covered by a section of the film, which is connected to the circumferential section of the film that is pressed into the cavity or the through-opening.

5. A method according to claim 1, comprising removing, after the pressing, a protruding section of the film so that the circumferential section of the film ends flush with a surface of the base body on one side of the base body.

6. A method according to claim 1, wherein the film is dimensioned such, after the pressing, that the film does not protrude from the cavity or the through-opening of the base body on one side of the base body.

7. A method according to claim 1, wherein the X-ray marker is spherical or cylindrical and the pressing deforms it into a half shell or disk shape.

8. A method according to claim 1, wherein the pressing is conducted with two clamping jaws that engage the X-Ray marker and film section on both sides to deform the X-ray marker a force-fit manner in the cavity or the through-opening.

9. The method according to claim 8, comprising controlling the clamping jaws in such a way that a final thickness (D) of the at least one X-ray marker corresponds to a wall thickness (W) of the base body.

10. A method according to claim 1, wherein the film consists of one of the following materials: a plastic material, a polymer, polyurethane, electrospun plastic, electrospun polyurethane, PTFE, or silicone.

11. A method according to claim 1, wherein the X-ray marker is made of a metallic material that is more noble than a metallic material of the base body.

12. A method according to claim 1, wherein the X-ray marker comprises or consists of one of the following materials: a radiopaque metallic material, gold, a gold alloy, platinum, or a platinum alloy.

13. A method according to claim 1, comprising fusing the film during or after the pressing.

14. The method according to claim 13, comprising pressing with a heated element to conduct the fusing with the pressing.

15. A method according to claim 1, wherein the arranging comprises
    initially arranging the film on a perforated plate including a plurality of holes, arranging a plurality of X-ray markers over the plurality of holes and pressing the plurality of X-ray markers with the film and then arranging the film with the plurality of X-ray markers over a plurality of receptacles in the base body and then conducting the pressing.

16. The method of claim 15, comprising coating the plurality of X-ray markers. with a plastic material.

17. The method of claim 16, wherein the plastic material comprises polyurethane.

18. The method of claim 15, wherein the initial arranging comprises arranging the plurality of X-ray markers between two layers of the film.

* * * * *